United States Patent
Uchida et al.

(10) Patent No.: US 9,352,082 B2
(45) Date of Patent: May 31, 2016

(54) FLUID SUPPLY APPARATUS

(71) Applicant: SEIKO EPSON CORPORATION, Tokyo (JP)

(72) Inventors: Kazuaki Uchida, Fujimi-machi (JP); Atsuya Hirabayashi, Chino (JP); Takeshi Seto, Chofu (JP); Takahiro Matsuzaki, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 246 days.

(21) Appl. No.: 14/074,434

(22) Filed: Nov. 7, 2013

(65) Prior Publication Data

US 2014/0134001 A1    May 15, 2014

(30) Foreign Application Priority Data

Nov. 12, 2012   (JP) ................................. 2012-248058

(51) Int. Cl.
*A61M 5/142*    (2006.01)
*A61B 17/3203*  (2006.01)
*F04B 11/00*    (2006.01)

(52) U.S. Cl.
CPC .......... *A61M 5/1422* (2013.01); *A61B 17/3203* (2013.01); *F04B 11/005* (2013.01)

(58) Field of Classification Search
CPC ...... F04B 1/02; F04B 11/005; F04B 11/0058; F04B 53/086; F04B 11/05; A61M 5/1422; A61B 17/3203
USPC ............................ 417/2, 8, 62, 216, 286, 426
See application file for complete search history.

(56) References Cited

U.S. PATENT DOCUMENTS

| | | | |
|---|---|---|---|
| 2007/0129680 A1 | 6/2007 | Hagg et al. | |
| 2009/0060764 A1* | 3/2009 | Mitzlaff ............. | A61B 17/3203 417/460 |
| 2011/0002802 A1* | 1/2011 | Capone .................... | F04B 7/00 417/486 |
| 2012/0046605 A1 | 2/2012 | Uchida et al. | |

FOREIGN PATENT DOCUMENTS

| | | |
|---|---|---|
| JP | 09-264261 | 10/1997 |
| JP | H09-264261 | 10/1997 |
| JP | 2010-075589 | 4/2010 |
| JP | 2010-084564 | 4/2010 |
| JP | 2010075589 A * | 4/2010 |

OTHER PUBLICATIONS

European Search Report for European Patent Application No. 13192132.2 dated Jan. 17, 2014.

* cited by examiner

*Primary Examiner* — Justin Jonaitis
*Assistant Examiner* — Christopher Brunjes
(74) *Attorney, Agent, or Firm* — Workman Nydegger (57) ABSTRACT

A fluid supply apparatus which supplies fluid to a medical apparatus includes: a pump mechanism including a first pump capable of a suction operation of the fluid after a feeding operation of the fluid, and a second pump capable of a suction operation of the fluid during the feeding operation and a feeding operation of the fluid during the suction operation; a flow path which includes an elastic member and which communicates with the first pump and the second pump and supplies the fluid to the medical apparatus; and a flow path deforming unit which deforms a part of the flow path. The flow path deforming unit starts first deformation of the flow path before the first pump switches from the feeding operation to the suction operation, and completes the first deformation and starts second deformation of the flow path during the feeding operation by the second pump.

15 Claims, 10 Drawing Sheets

FLUID SUPPLY APPARATUS

This application claims priority to Japanese Patent Application No. 2012-248058 filed on Nov. 12, 2012. The entire disclosure of the Japanese Patent Application No. 2012-248058 is hereby incorporated herein by reference.

BACKGROUND

1. Technical Field

The present invention relates to a technique for supplying fluid to a medical apparatus.

2. Related Art

According to a related art, for example, a technique disclosed in JP-A-9-264261 is known as a technique for stably feeding fluid. JP-A-9-264261 discloses a technique in which when one of two plunger pumps is carrying out an ejection process at a predetermined ejection pressure, the other stands by in the state of pre-pressurizing the fluid, and when the ejection pressure of the one plunger pump begins to fall, the other starts a pressurization and ejection process of the fluid and raises the pressure to a target ejection pressure within a short time, thus carrying out ejection continuously.

However, in the technique of JP-A-9-264261, a periodic pulsating flow is generated when the ejection is switched between the two plunger pumps. For example, in the case where the technique is applied to a fluid supply apparatus which feeds fluid to a water jet knife as a medical apparatus, a problem is pointed out that a pulsating flow is generated in the fluid ejected from the water jet knife, which is undesirable to the operation of the water jet knife. Also, various other issues are pointed such as reduction in size of the device, reduction in cost, resource saving, easier manufacturing, and improvement in user-friendliness. Such problems are equally seen in devices for supplying fluid not only to a water jet knife but also to other medical apparatuses.

SUMMARY

An advantage of some aspects of the invention is to solve at least a part of the problems described above, and the invention can be implemented as the following aspects.

(1) An aspect of the invention provides a fluid supply apparatus which supplies fluid to a medical apparatus. The fluid supply apparatus includes: a pump mechanism having a first pump capable of carrying out a suction operation of the fluid after a feeding operation of the fluid, and a second pump capable of carrying out a suction operation of the fluid during the feeding operation by the first pump and carrying out a feeding operation of the fluid during the suction operation by the first pump; a flow path which includes an elastic member and which communicates with the first pump and the second pump and supplies the fluid to the medical apparatus; and a flow path deforming unit which deforms a part of the flow path. The flow path deforming unit starts first deformation of the flow path before the first pump switches from the feeding operation to the suction operation, and completes the first deformation of the flow path and starts second deformation of the flow path during the feeding operation by the second pump. According to the fluid supply apparatus of this embodiment, by deforming the flow path, fluctuation in the flow rate of the fluid supplied to the medical apparatus can be restrained.

(2) The fluid supply apparatus of the aspect described above may be configured such that an amount of deformation of the flow path by the flow path deforming unit has a peak during a period from when an amount of fluid fed per unit time by the first pump reaches a predetermined amount of fluid fed, until the amount of fluid fed per unit time becomes smaller than the predetermined amount of fluid fed. According to the fluid supply apparatus of this aspect, the deforming operation by the flow path deforming unit may be set based on the amount of fluid fed by the first pump, in order to properly set the timing when the flow path deforming unit deforms the flow path most. For example, by aligning the control of the flow path deforming unit with the control of the first pump, fluctuation in the flow rate of the fluid supplied to the medical apparatus can be restrained. The control of the flow path deforming unit may also be aligned with the control of the second pump. By such easy setting of the deforming operation by the flow path deforming unit, fluctuation in the flow rate of the fluid supplied to the medical apparatus can be restrained.

(3) The fluid supply apparatus of the aspect described above may be configured such that a speed at which the flow path deforming unit deforms the flow path is the fastest when the first pump switches from the feeding operation to the suction operation. According to the fluid supply apparatus of this aspect, when the amount of fluid fed per unit time by the first pump is the minimum, the speed of deforming the flow path is made the fastest. Thus, fluctuation in the flow rate of the fluid supplied to the medical apparatus can be restrained.

(4) The fluid supply apparatus of the aspect described above may be configured such that the second pump shifts from the suction operation to the feeding operation when the first pump shifts from the feeding operation to the suction operation. According to the fluid supply apparatus of this aspect, the operation control of the pumps can be simplified.

(5) The fluid supply apparatus of the aspect described above may be configured such that, where a period from when the first pump starts the feeding operation until the suction operation ends is T, a deformation period of the flow path deformed by the flow path deforming unit is T/2 or shorter. According to the fluid supply apparatus of this aspect, fluctuation in the flow rate generated within the period T/2 can be restrained.

(6) The fluid supply apparatus of the aspect described above may be configured such that the flow path deforming unit deforms the flow path by pressing an outer wall surface of the flow path. According to the fluid supply apparatus of this aspect, the flow path can be deformed by a relatively simple method.

(7) The fluid supply apparatus of the aspect described above may be configured such that the flow path includes a first flow path connected to the first pump, a second flow path connected to the second pump, and a third flow path which is a flow path into which the first flow path and the second flow path join together and which is connected to the medical apparatus, and the flow path deforming unit deforms the third flow path. According to the fluid supply apparatus of this aspect, since only one flow path deforming unit is provided, simplified control can be realized.

(8) The fluid supply apparatus of the aspect of the invention may be configured such that the flow path deforming unit blocks the flow path by deforming the flow path and thus stops supply of the fluid from the first pump and the second pump to the medical apparatus. According to the fluid supply apparatus of this aspect, supply of the fluid can be stopped by the flow path deforming unit.

(9) The fluid supply apparatus of the aspect may be configured such that the medical apparatus is a therapeutic apparatus which ejects fluid to a living body and thus treats the living body. According to the fluid supply apparatus of this aspect, the medical apparatus which ejects the fluid can be supplied with the fluid at a stable flow rate.

(10) Another aspect of the invention provides a fluid supply apparatus which supplies fluid to a medical apparatus. The fluid supply apparatus includes: a pump mechanism having plural pumps which carry out a feeding operation to feed the fluid outside; a flow path which is elastic and supplies the fluid fed from each of the pumps to the medical apparatus; and a flow path deforming unit which deforms the flow path at a predetermined timing that is set in advance. According to this fluid supply apparatus, by setting the timing when pressure fluctuation of the fluid supplied to the medical apparatus as the predetermined timing of deforming the flow path, fluctuation in the flow rate of the fluid supplied to the medical apparatus can be restrained.

The invention can be realized in various embodiments. For example, the invention can be realized in such forms as a water jet knife system, fluid supply system, fluid supply method, pump control method and pulsating flow control method.

BRIEF DESCRIPTION OF THE DRAWINGS

The invention will be described with reference to the accompanying drawings, wherein like numbers reference like elements.

DESCRIPTION OF EXEMPLARY EMBODIMENTS

A. First Embodiment

A1. System Configuration

Figure 1:
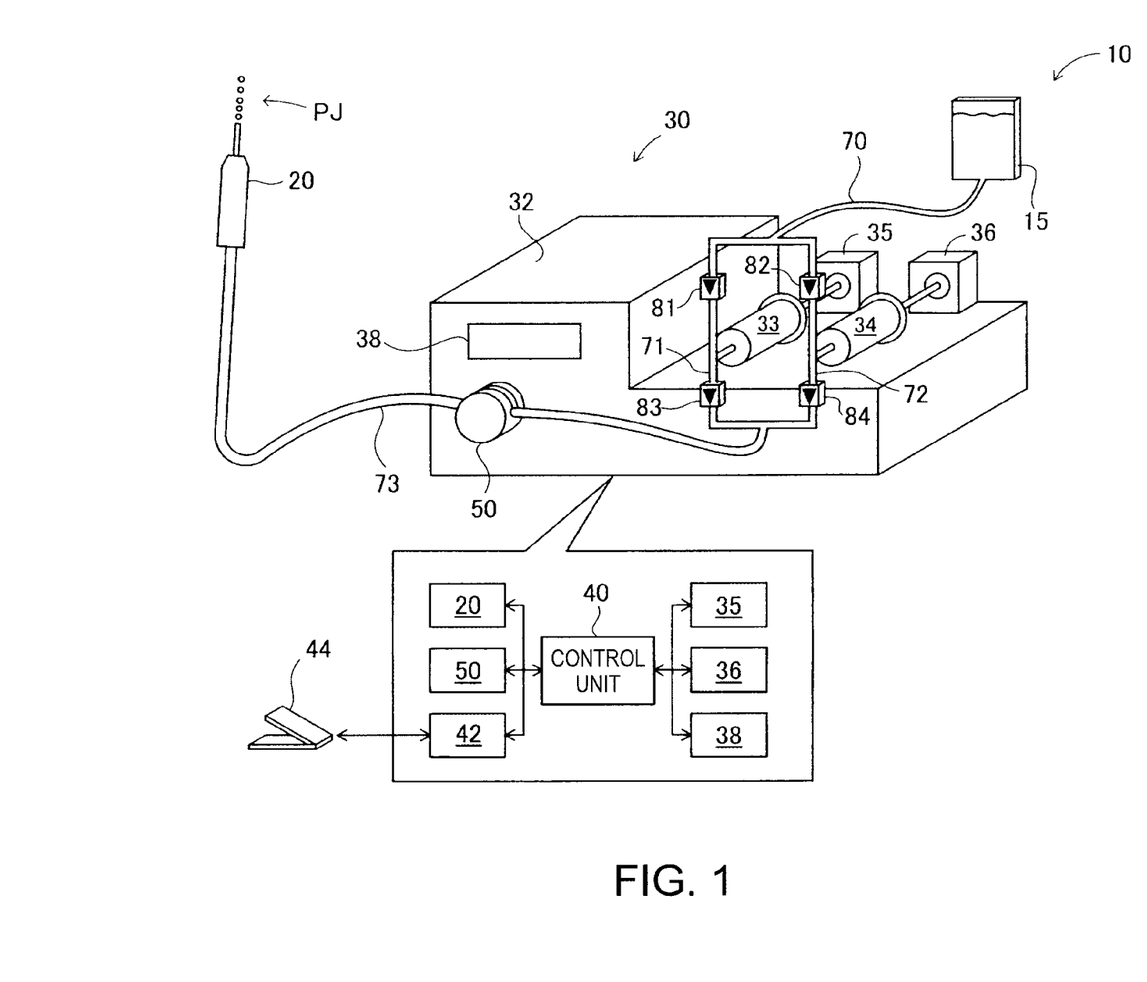
FIG. 1 is an explanatory view showing a water jet knife system.

FIG. 1 is an explanatory view illustrating a water jet knife system 10 using a fluid supply apparatus as a first embodiment of the invention. A water jet knife is a kind of surgical knife and ejects fluid at a high pressure to perform incision and excision with the ejection pressure. In this embodiment, a physiological saline solution, Ringer's solution, water or the like is employed as fluid to be ejected.

The water jet knife system 10 has a water jet knife 20, a fluid supply apparatus 30 which supplies water to the water jet knife 20, and a fluid storage unit 15 which stores water to be supplied to the water jet knife 20. The water jet knife 20 has, inside itself, a mechanism which generates a pulse water flow using a piezoelectric element as a power source. In the water jet knife 20, the piezoelectric element is driven at a predetermined frequency to eject water supplied from the fluid supply apparatus 30 to outside as a pulsed high-pressure jet water flow (pulse jet PJ). The structure of the water jet knife 20 will be described in detail later.

The water jet knife 20, the fluid supply apparatus 30, and the fluid storage unit 15 are connected with each other via flow paths 70 to 73. Specifically, the fluid storage unit 15 is connected to one end of the flow path 70. The other end of the flow path 70 is connected to diverge into the flow path 71 and the flow path 72. The flow path 71 is connected to a plunger pump 33 provided in the fluid supply apparatus 30. The flow path 72 is connected to a plunger pump 34 provided in the fluid supply apparatus 30. The flow path 71 and the flow path 72 join together and are connected to the flow path 73. The flow path 73 is connected to the water jet knife 20.

The water in the fluid storage unit 15 is supplied to the water jet knife 20 via the flow paths 70 to 73 by the operation of the fluid supply apparatus 30. Check valves 81 to 84 are provided in the flow paths 71, 72. The water circulating through the flow paths 70 to 73, by the function of the check valves 81 to 84, circulates only in one direction from the fluid storage unit 15 toward the water jet knife 20. The flow paths 70 to 73 are tubes made of polyvinyl chloride and are elastic. As the flow paths 70 to 73, elastic tubes made of silicone, thermoplastic elastomer or the like may also be employed.

The fluid supply apparatus 30 has a casing 32, plunger pumps 33, 34, pump drive units 35, 36, a display unit 38, and a flow path deforming mechanism 50. The plunger pumps 33, 34 carry out a suction operation to suck water from the fluid storage unit 15 and a feeding operation to feed the sucked water to the water jet knife 20. The pump drive units 35, 36 function as a power source for the plunger pumps 33, 34 to carry out the suction operation and the feeding operation. The pump drive units 35, 36 have a motor as a power source and thus realize the suction operation and the feeding operation by the plunger pumps 33, 34.

The display unit 38 is a display unit which displays various kinds of information about the supply of water, such as the amount of water supplied to the water jet knife 20 by the fluid supply apparatus 30, and the flow speed. The flow path deforming mechanism 50 is a mechanism which holds the flow path 73 therein and deforms the flow path 73 at the predetermined timing. The flow path deforming mechanism 50 will be described in detail later.

As illustrated, the fluid supply apparatus 30 has a control unit 40 inside the casing 32. The control unit 40 is connected to the water jet knife 20, the pump drive units 35, 36, the display unit 38, an input/output IF 42, and the flow path deforming mechanism 50, and controls the operation of each device. A foot switch 44 for a user to operate ejection and stop of water from the water jet knife 20 is connected to the input/output IF 42. As the user operates the foot switch 44, the control unit 40 causes the water jet knife 20 and the fluid supply apparatus 30 (pump drive units 35, 36) to operate synchronously. Specifically, when the user uses the foot switch 44 to carry out an operation to eject a pulse jet PJ from the water jet knife 20, the control unit 40 drives the pump drive units 35, 36 and thus causes the water jet knife 20 to supply water, and the control unit 40 also controls the water jet knife 20 to eject the supplied water to outside as a pulse jet PJ.

Figure 2:
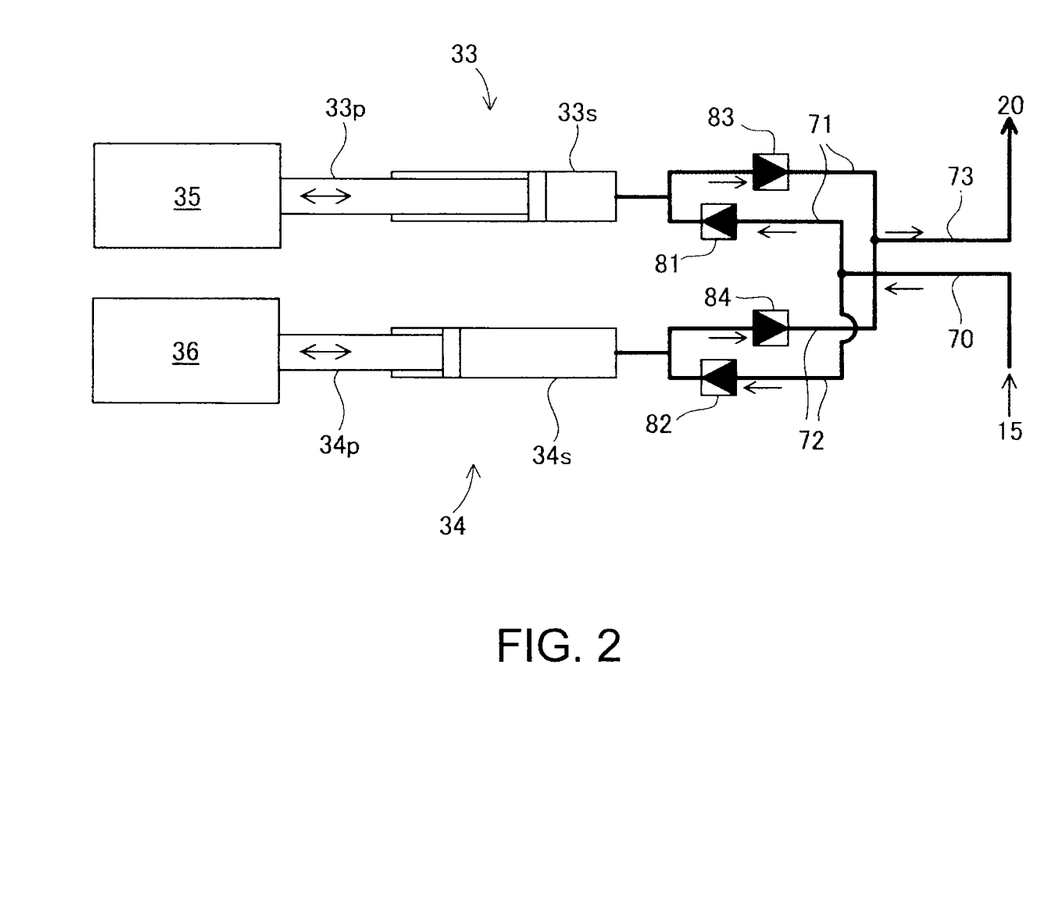
FIG. 2 is an explanatory view showing supply of water by a fluid supply apparatus.

FIG. 2 is an explanatory view illustrating the supply of water by the fluid supply apparatus 30. FIG. 2 shows a configuration involved in the circulation of water, mainly around plunger pumps 33, 34. As illustrated, the plunger pump 33 has a syringe 33s and the plunger 33p. Similarly, the plunger pump 34 has a syringe 34s and a plunger 34p. The plunger 33p and the plunger 34p are attached to the pump drive unit 35 and the pump drive unit 36, respectively.

The pump drive units 35, 36 push and pull the plunger 33p and the plunger 34p, respectively, to cause plungers to reciprocate. As illustrated, an operation in which the plunger 33p (34p) is pushed into the syringe 33s (34s) is called a feeding operation of the plunger pump 33 (34). Meanwhile, an operation in which the plunger 33p (34p) is pulled out of the syringe 33s (34s) is called a suction operation of the plunger pump 33 (34). The plunger pumps 33, 34 function as displacement pumps with the power of the pump drive units 35, 36.

The flow path 71 is connected to the plunger pump 33. The flow path 72 is connected to the plunger pump 34. When the plunger pump 33 carries out the suction operation, the water in the fluid storage unit 15 is sucked into the syringe 33s via the flow path 70, the flow path 71, and the check valve 81. When the plunger pump 33 carries out the feeding operation, the water in the syringe 33s is fed to the water jet knife 20 via the check valve 83, the flow path 71, and the flow path 73. The suction operation and the feeding operation carried out by the plunger pump 34 are based on similar principles to the plunger pump 33 and therefore will not be described further in detail.

Figure 3A:
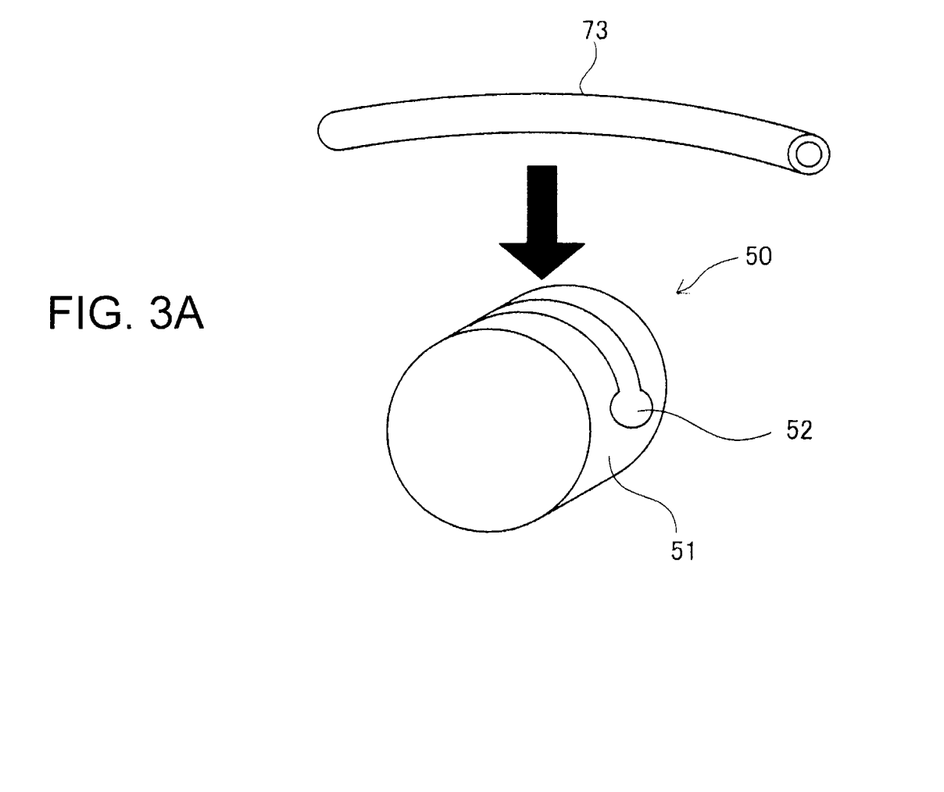
FIGS. 3A and 3B are explanatory views showing a flow path deforming mechanism.
Figure 3B:
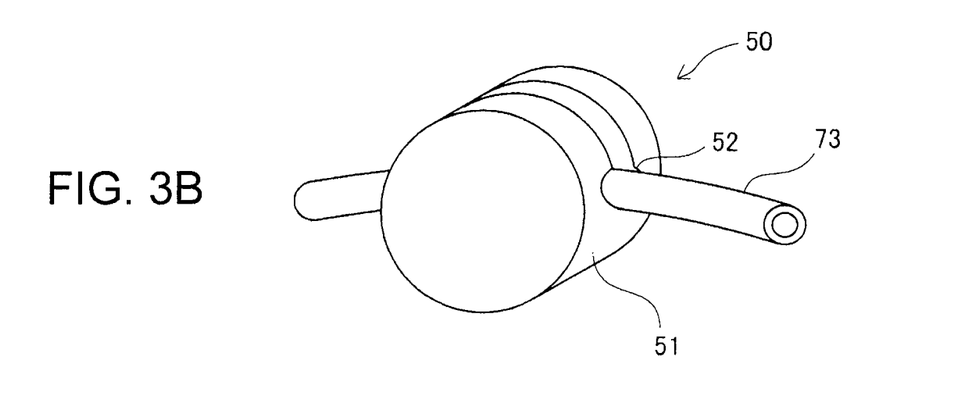

Next, the flow path deforming mechanism 50 provided in the fluid supply apparatus 30 will be described. FIGS. 3A and 3B are explanatory views illustrating the flow path deforming mechanism 50. The flow path deforming mechanism 50 has a flow path fixing portion 51 which can be observed from outside, and a pressing mechanism 53 (later described) formed inside the casing 32. FIGS. 3A and 3B show the flow path fixing portion 51 which can be observed from outside. A groove portion 52 for holding the flow path 73 therein is formed in the flow path fixing portion 51. When using the water jet knife system 10, the user fits the flow path 73 into the groove portion 52 as shown in FIGS. 3A and 3B.

Figure 4A:
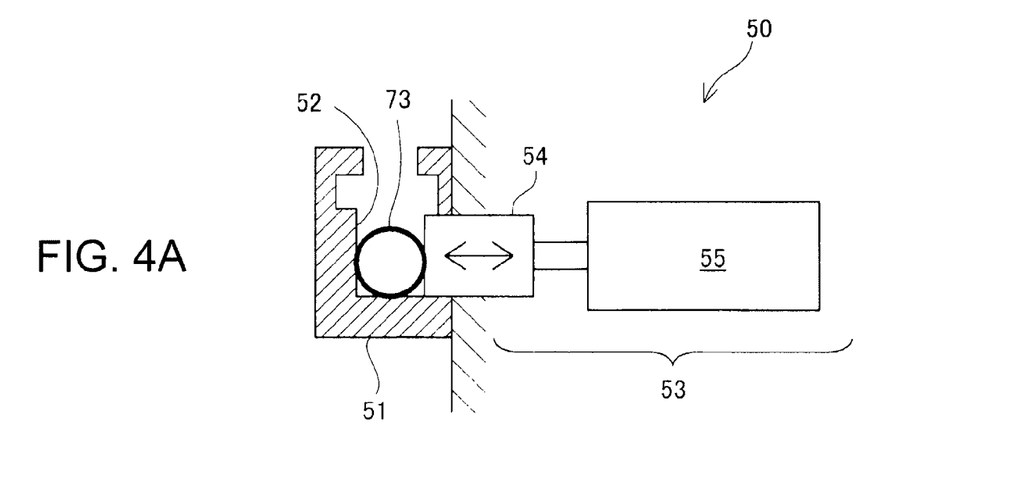
FIGS. 4A and 4B are explanatory views showing the structure of the flow path deforming mechanism.
Figure 4B:
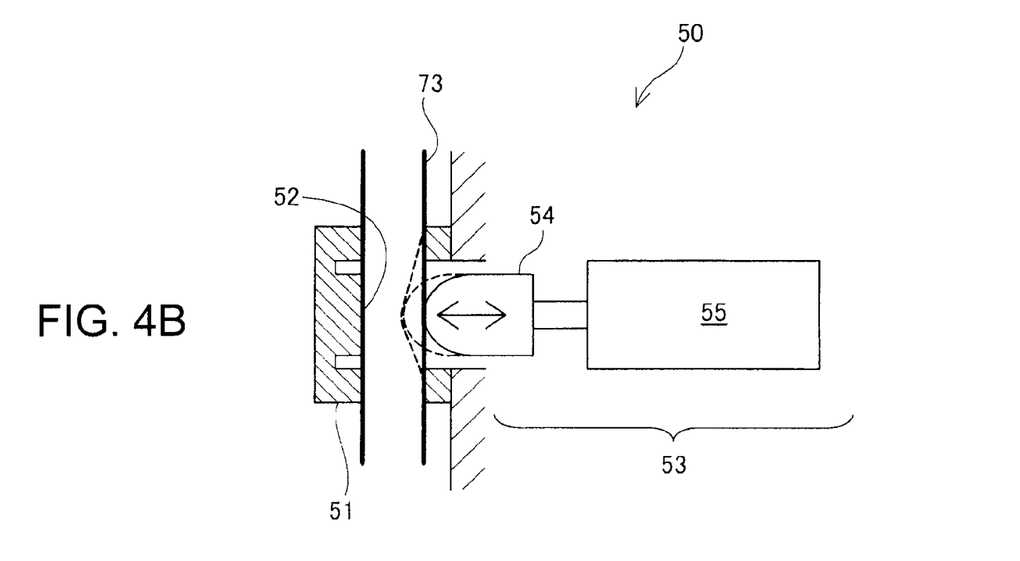

FIGS. 4A and 4B are explanatory views illustrating the structure of the flow path deforming mechanism 50, including portions formed inside the casing 32. FIG. 4A is an explanatory view showing a vertical sectional structure of the flow path deforming mechanism 50. FIG. 4B is an explanatory view showing a horizontal sectional structure of the flow path deforming mechanism 50. The flow path deforming mechanism 50 has the above flow path fixing portion 51 and also has a pressing mechanism 53 inside the casing 32. The pressing mechanism 53 has a pressing portion 54 to press the flow path 73, and a linear actuator 55 which applies a pressing force to the pressing portion 54. As illustrated, the linear actuator 55 is horizontally driven in a direction of pressing the flow path 73 (hereinafter also referred to as a pressing direction). The horizontal driving of the linear actuator 55 causes the pressing portion 54 to press a wall surface of the flow path 73. As shown in FIG. 4B, the surface of the pressing portion 54 that contacts the flow path 73 is a curved surface and thus restrains damage to the flow path 73 by the pressing. However, this surface is not limited to a curved surface and may be any surface that does not damage the flow path 73. Also, with respect to the medical apparatus, in many cases, the flow path 73 that is used once for treatment is disposed of in view of hygiene. Therefore, every time the apparatus is used, the pressing portion 54 presses a new flow path 73. Thus, the possibility that the pressing by the pressing portion 54 can damage the flow path 73 is extremely low.

As shown in FIG. 4B, when the pressing mechanism 53 presses the flow path 73, the flow path 73 is locally deformed. When water is circulating in the flow path 73, the pressure inside the flow path 73 is increased by the pressing with the pressing mechanism 53. When water is supplied to the water jet knife 20 from the fluid supply apparatus 30, the control unit 40 drives the pressing mechanism 53 and restrains the pressure fluctuation of the water supplied to the water jet knife 20 (pressure fluctuation restraint). The pressure fluctuation restraint will be described hereinafter.

A2. Pressure Fluctuation Restraint

Figure 5A:
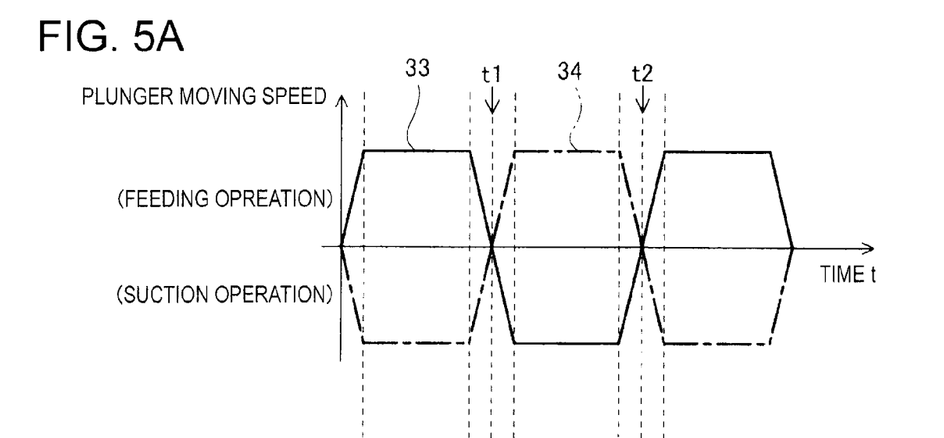
FIGS. 5A to 5C are explanatory views showing the operation of plunger pumps and the flow path deforming mechanism.
Figure 5B:
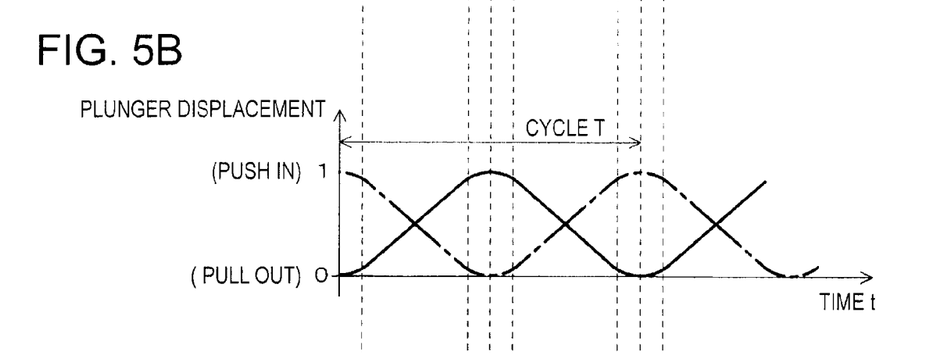
Figure 5C:
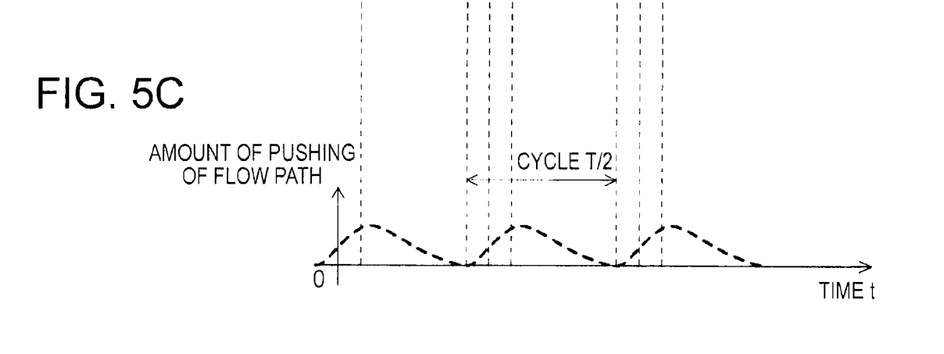

FIGS. 5A to 5C are explanatory views illustrating the operation of the plunger pumps 33, 34 and the flow path deforming mechanism 50 under the control of the control unit 40 when the fluid supply apparatus 30 supplies water to the water jet knife 20. FIG. 5A shows the moving speed of the plungers 33p, 34p. The solid line on the graph shows the moving speed of the plunger 33p. The chain dotted line shows the moving speed of the plunger 34p. In the graph corresponding to each plunger pump (33, 34), the portion along values 0 and above on the vertical axis corresponds to the feeding operation, and the portion below 0 corresponds to the suction operation. The horizontal axis represents time. In this embodiment, the control unit 40 controls the operation time of the feeding operation and the operation time of the suction operation of each plunger pump. When the plunger pump 33 carries out the feeding operation, the plunger pump 34 carries out the suction operation. It is desirable that the plunger pump 33 and the plunger pump 34 have the same amount of fluid fed per unit time. However, a difference of approximately ±5% is allowable. The control unit 40 also performs control so that only one of the two plunger pumps constantly carries out the feeding operation. The operation control of the plunger pumps by the control unit 40 is carried out indirectly as the control unit 40 controls the driving of the pump drive units 35, 36. As for the suction operation by the plunger pumps 33, 34, while one plunger pump carries out the feeding operation, the other plunger pump may carry out the suction operation. The moving speeds of the plungers 33p, 34p need not be equal as shown in FIG. 5A. The operation time of the feeding operation and the operation time of the suction operation by each plunger pump need not be the same, either.

FIG. 5B shows displacement of each plunger 33p, 34p in the case where each plunger pump 33, 34 carries out the operation shown in FIG. 5A. The state where the plungers 33p, 34p are pulled out to the maximum from the syringes 33s, 34s corresponds to "0" on the vertical axis of the graph of FIG. 5B. The state where the plungers 33p, 34p are pushed to the maximum into the syringes 33s, 34s corresponds to "1" on the vertical axis of the graph of FIG. 5B. The vertices corresponding to maximum and minimum values on each graph curve corresponding to the syringes 33s, 34s are shown as gentler curves than the actual curves, in order to facilitate understanding of the explanation. However, the actual curves are steeper.

FIG. 5C shows the operation of the flow path deforming mechanism 50. The vertical axis on the illustrated graph represents the amount of pushing on the flow path 73 when the flow path deforming mechanism 50 presses the flow path 73. The value 0 on the vertical axis indicates that the flow path deforming mechanism 50 is not pushing in the flow path 73. The horizontal axis on the graph represents time. In this embodiment, the control unit 40 controls the operation of the flow path deforming mechanism 50 in such a way that the speed at which the flow path deforming mechanism 50 pushes in the flow path 73 reaches the maximum (the slope of the graph reaches the maximum) at timings t1, t2 in FIG. 5A. The timings t1, t2 in FIG. 5A are the timings when the plunger pump starts the feeding operation.

Figure 6A:
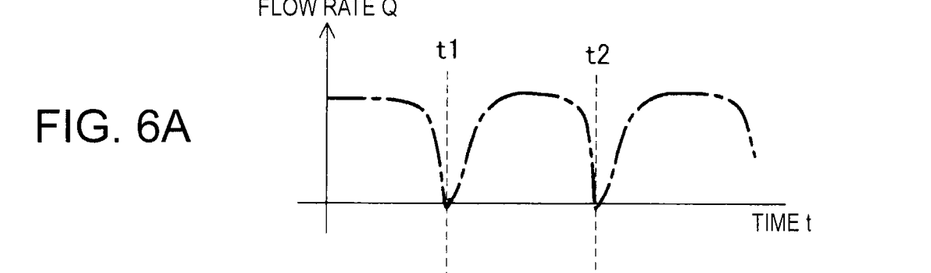
FIGS. 6A to 6C are explanatory views showing the flow rate of water supplied to a water jet knife.
Figure 6B:
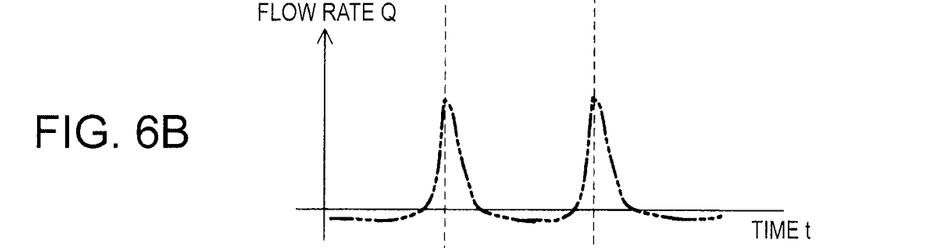
Figure 6C:
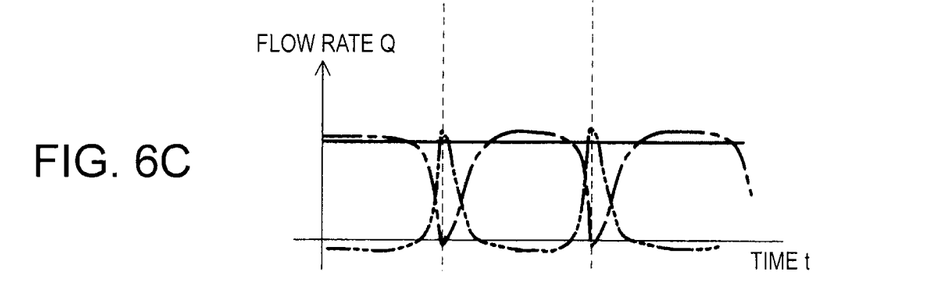

FIGS. 6A to 6C are explanatory views showing change in the flow rate of water supplied from the flow path 73 to the water jet knife 20 by the operation of the plunger pumps 33, 34 and the flow path deforming mechanism 50 described with reference to FIGS. 5A to 5C. FIG. 6A shows how the flow rate of water in the flow path 73 changes due to the operation of the two plunger pumps 33, 34. As illustrated, the flow rate of water supplied from the flow path 73 to the water jet knife 20 decreases at the timings t1, t2 when each plunger pump 33, 34 starts the feeding operation. It can be considered that this is because the moving speed of the plunger decreases around the time when the plunger pump switches between the feeding operation and the suction operation, causing a reduction in the feeding pressure of water from the plunger pump to the flow path 73.

Also, when the plunger pumps are driven in such a way that the rise time and fall time of fluid feeding become equal, as shown in FIG. 5A, the flow rate of water that actually flows through the flow path reaches the minimum value at t1, t2, but the curve along time is not symmetrical about t1, t2 and the rise is delayed with respect to the fall, as shown in FIG. 6A. This is because, due to the influence of air bubbles in the flow path and the elastic action of the flow path or the like, the feeding pressure does not necessarily rise in proportion to the plunger moving speed and has a temporal delay.

FIG. 6B shows how the flow rate of water in the flow path 73 changes due to the operation of the flow path deforming mechanism 50. As illustrated, it can be seen that the flow rate reaches the maximum at the timings t1, t2. This is because the control unit 40 controls the operation of the flow path deforming mechanism 50 in such a way that the speed at which the flow path deforming mechanism 50 pushes in the flow path 73 reaches the maximum at the timings t1, t2.

Also, as shown in FIG. 6B, it can be seen that the change in the flow rate of water in the flow path 73 due to the operation of the flow path deforming mechanism 50 is not symmetrical about the timings t1, t2 but is steep during the rise and gentle during the fall. This is because the control unit 40 controls the operation of the flow path deforming mechanism 50 in such a way that the amount of pushing by which the flow path deforming mechanism 50 pushes in the flow path 73 reaches the maximum after the amount of fluid fed per unit time by the pump reaches a predetermined amount of fluid fed.

According to the above control, the change in the flow rate of water in the flow path 73 due to the operation of the flow path deforming mechanism 50 reaches the maximum at the timings t1, t2 and is steep during the rise and gentle during the fall. Therefore, this change is in a compensatory relation with the change in the flow rate shown in FIG. 6A, which reaches the minimum at the timings t1, t2 when the pumps are switched, and which is steep during the fall and gentle during the rise. When the two changes in the flow rate are superimposed, water flows through the flow path 73 at a substantially constant flow rate having little change with time.

FIG. 6C shows a flow rate in the case where the change in the flow rate in the flow path 73 due to the operation of the plunger pumps 33, 34, and the change in the flow rate in the flow path 73 due to the operation of the flow path deforming mechanism 50 are superimposed. That is, the illustrated graph shows the change in the flow rate in the flow path 73 when the fluid supply apparatus 30 is actually supplying water to the water jet knife 20. The chain dotted line on the graph shows the change in the flow rate in the flow path 73 due to the operation of the plunger pumps 33, 34. The double-chain dotted line shows the change in the flow rate in the flow path 73 due to the operation of the flow path deforming mechanism 50. The solid line shows a flow rate obtained by superimposing these two flow rates. As illustrated, it can be seen that fluctuation in the flow rate as a result of the superimposition is restrained. That is, the pressurization of the flow path 73 by the flow path deforming mechanism 50 compensates for the amount of fall in the pressure of water in the flow path 73 due to the operation of the plunger pumps 33, 34. Since the fluctuation in the pressure in the flow path 73 is restrained, the fluctuation in the flow rate of water in the flow path 73 is restrained. In this manner, the control unit 40 restrains the pressure fluctuation in the flow path 73 due to the operation of the plunger pumps 33, 34 by controlling the operation of the flow path deforming mechanism 50.

Also, since the flow path deforming mechanism 50 needs to deform the flow path 73 every time each plunger is switched, the duration of the deformation of the flow path 73 by the flow path deforming mechanism 50 is equal to or shorter than the operation time of the feeding operation by each plunger.

In this example, the operation time of the feeding operation and the operation time of the suction operation by each plunger are controlled to be equal. Therefore, if one feeding operation by each plunger and one subsequent suction operation form a cycle and the cycle time is T, the duration of the deformation of the flow path 73 by the flow path deforming mechanism 50 needs to be equal to or shorter than T/2.

In this embodiment, a program corresponding to the operation of the flow path deforming mechanism 50 is stored in a storage unit provided in the control unit 40. The control unit 40 causes the flow path deforming mechanism 50 to operate according to this program. Also, the control unit 40 may estimate an optimum operation of the flow path deforming mechanism 50 based on the moving speed of the plunger pump 33 and the plunger pump 34 while the fluid supply apparatus 30 is in operation, and may cause the flow path deforming mechanism 50 to operate according to the result of the estimate. In any of these cases, the operation control of the flow path deforming mechanism. 50 is included in the control to "cause the flow path deforming mechanism 50 to operate at a predetermined timing that is set in advance".

A3. Water Jet Knife

Figure 7:
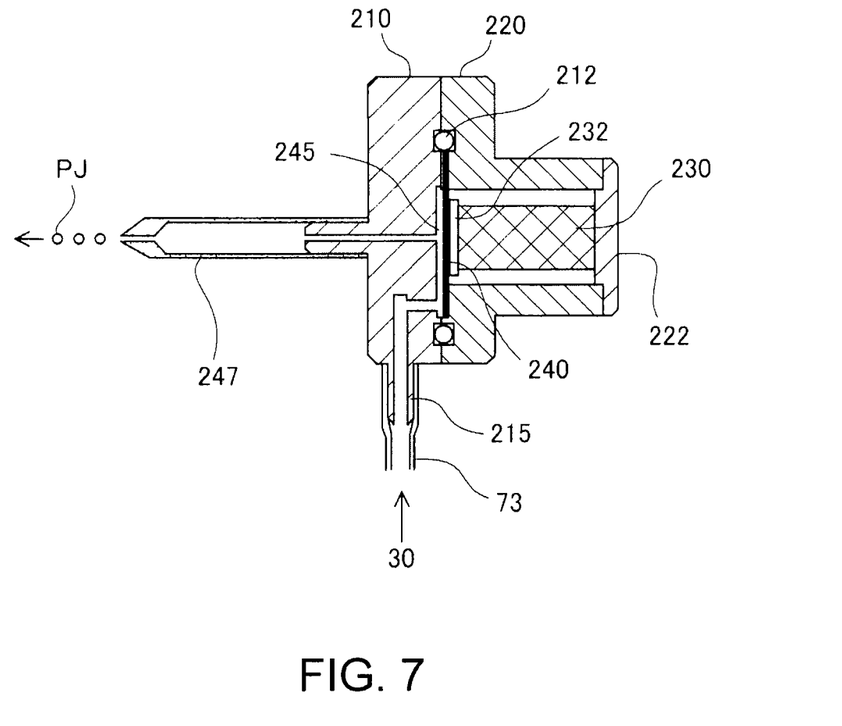
FIG. 7 is an explanatory view showing the structure of the water jet knife.

Next, the water jet knife 20 will be described. FIG. 7 is an explanatory view illustrating the structure of the water jet knife 20. The water jet knife 20 has an upper case 210, a lower case 220, a bottom portion 222, a piezoelectric element 230, an upper plate 232, a diaphragm 240, a packing 212, and a nozzle 247. The upper case 210 and the lower case 220 are joined together, facing each other. The lower case 220 is a cylindrical member and one end thereof is airtightly closed by the bottom portion 222. As illustrated, the piezoelectric element 230 is arranged in an inner space of the lower case 220.

The piezoelectric element 230 is a multilayer piezoelectric element and forms an actuator. One end of the piezoelectric element 230 is fixed to the diaphragm 240 via the upper plate 232. The other end of the piezoelectric element 230 is fixed to the bottom portion 222. The diaphragm 240 is made of a disc-shaped metal thin film and a circumferential edge thereof is fixed to the lower case 220. A pump chamber 245 is formed between the diaphragm 240 and the upper case 210 and the volume thereof changes as the piezoelectric element 230 is driven.

In the upper case 210, a flow path connecting portion 215 for connecting a flow path is formed. The flow path 73 is connected to the flow path connecting portion 215. The water supplied from the fluid supply apparatus 30 is supplied to the pump chamber 245 via the flow path 73 and the flow path connecting portion 215. When the piezoelectric element 230 oscillates at a predetermined frequency, the volume of the pump chamber 245 changes via the diaphragm 240 and the stored water is pressurized. The pressurized water is ejected through the nozzle 247 attached to the upper case 210.

Oscillation control of the piezoelectric element 230 is carried out by a control unit (not shown) of the water jet knife 20. As the control unit controls the oscillation of the piezoelectric element 230, the water jet knife 20 can eject pulse jets PJ in various forms. Up to this point is the explanation of the configuration of the water jet knife 20.

As described above, the fluid supply apparatus 30 can restrain pressure fluctuation of supplied water by causing the flow path deforming mechanism 50 to operate. As a result, flow rate fluctuation of the water supplied to the water jet knife 20 can be restrained. The fluid supply apparatus 30 can restrain pressure fluctuation by a relatively simple method such as deforming a flow path. The operation of the flow path deforming mechanism 50 is carried out at a predetermined timing that is set in advance and therefore can be controlled easily. Also, the predetermined timing when the flow path deforming mechanism 50 is made to operate has a correlation with the timing when the plunger pumps 33, 34 start each feeding operation. Therefore, pressure fluctuation based on the feeding operation by the plunger pumps 33, 34 can be restrained.

In the water jet knife system 10, the number of plunger pumps is two. Therefore, a simplified structure and reduced cost can be realized. Also, in the water jet knife system 10, the flow path 73 into which the flow path 71 and the flow path 72 join together is pressed by the flow path deforming mechanism 50, thus restraining pressure fluctuation. Therefore, pressure fluctuation can be restrained simply by pressing a part of the flow path. As a result, the pressure fluctuation restraint can be realized simply by providing one flow path deforming mechanism 50. Thus, simplified control and structure and reduced cost can be realized.

Also, in this embodiment, a water jet knife is employed as a medical apparatus to which the fluid supply apparatus 30 supplies fluid. In the water jet knife, supply of water with a stable flow rate is required. Therefore, by employing the fluid supply apparatus 30 as a fluid supply apparatus for supplying fluid to the water jet knife, it is possible to supply water under stable pressure and at a stable flow rate, and characteristics of the fluid supply apparatus 30 can be exhibited to the maximum.

B. Modifications

The invention is not limited to the above embodiments and can be carried out in various embodiments without departing from the scope of the invention. For example, the following modifications are possible.

B1. Modification 1

In the above embodiments, the fluid supply apparatus 30 has two plunger pumps. However, plunger pumps may be provided in an arbitrary number equal to two or greater, such as three or four, as long as these plunger pumps can be installed in the fluid supply apparatus 30. Also, the timing of the suction operation and the feeding operation of each of the plural plunger pumps is not limited to the timing described with reference to FIGS. 5A to 5C, and various timings can be employed. For example, the timings of the feeding operations of the plural plunger pumps may overlap each other. Even in such a case, the timing of internal pressure fluctuation caused by the feeding operation buy the plunger pumps can be acquired by measurement in advance and the control unit 40 can cause the flow path deforming mechanism 50 to operate according to the acquired timing, to supply water to the water jet knife 20 at a stable flow rate.

Figure 8A:
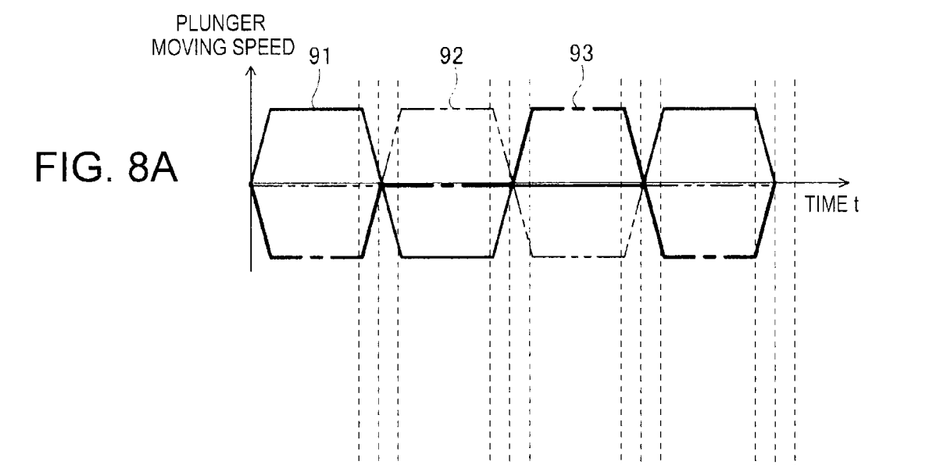
FIGS. 8A to 8C are explanatory views illustrating Modification 1.
Figure 8B:
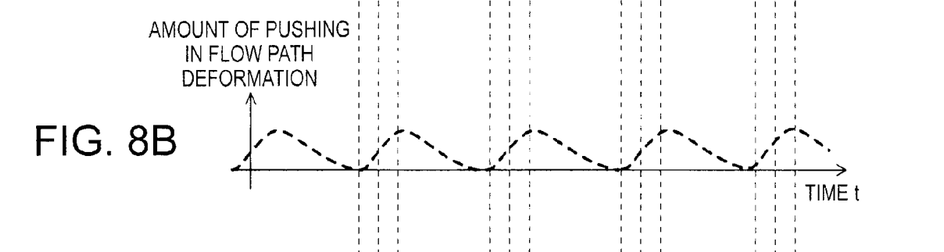
Figure 8C:
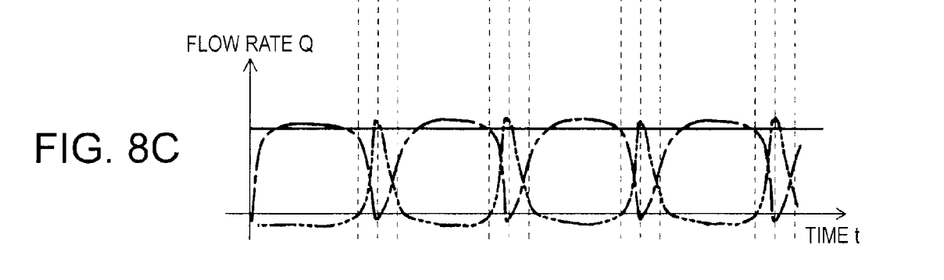

FIGS. 8A to 8C are explanatory views illustrating the case where the fluid supply apparatus 30 has three plunger pumps 91, 92, 93, as an example of Modification 1. FIG. 8A shows the moving speed of the plunger pumps 91, 92, 93. As illustrated, at any time, only one of the respective plunger pumps caries out the feeding operation. Each plunger pump carries out the feeding operation following a standby state after the suction operation.

FIG. 8B shows the amount of pushing on the flow path by the flow path deforming mechanism 50. As in the foregoing embodiment, the control unit 40 controls the operation of the flow path deforming mechanism 50 in such a way that the speed at which the flow path deforming mechanism 50 pushes in the flow path reaches the maximum at the timing when each plunger pump starts the feeding operation.

FIG. 8C shows change in flow rate in the flow path when the fluid supply apparatus 30 actually supplies water to the water jet knife 20. The chain dotted line on the graph shows change in the flow rate due to the operation of the plunger pumps 91, 92, 93. The double-chain dotted line shows change in the flow rate due to the operation of the flow path deforming mechanism 50. The solid line shows the flow rate in the case where these two rates are superimposed. As illustrated, it can be seen that fluctuation in the superimposed flow rate is restrained. Thus, similar effects to the foregoing embodiment can be achieved. In the foregoing embodiment and this modification, the flow path deforming mechanism 50 is made to operate in such a way that the speed at which the flow path deforming mechanism 50 pushes in the flow path reaches the maximum at the timing when each plunger pump starts the feeding operation. However, the flow path deforming mechanism 50 may be made to operate at various timings. If pressure fluctuation characteristics can be known based on characteristics of the fluid supply apparatus 30, the flow path deforming mechanism 50 may be made to operate at a timing corresponding to the characteristics to restrain pressure fluctuation.

B2. Modification 2

Figure 9A:
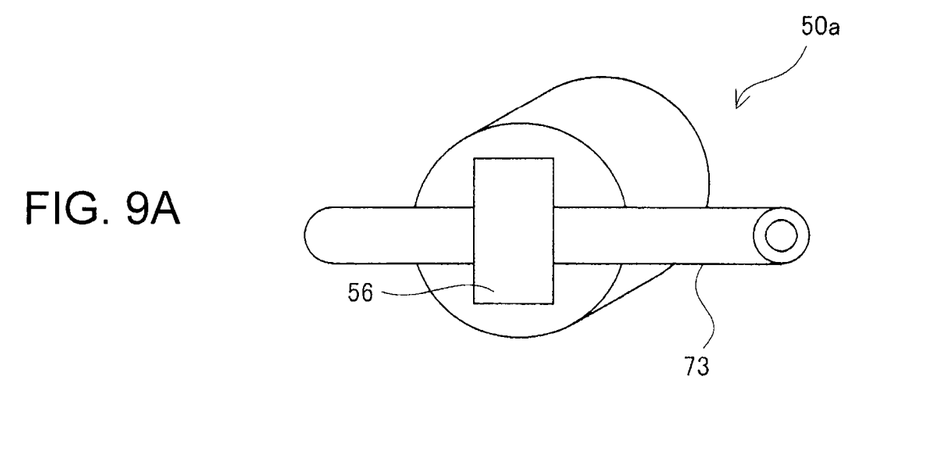
FIGS. 9A to 9C are explanatory views showing a flow path deforming mechanism.
Figure 9B:
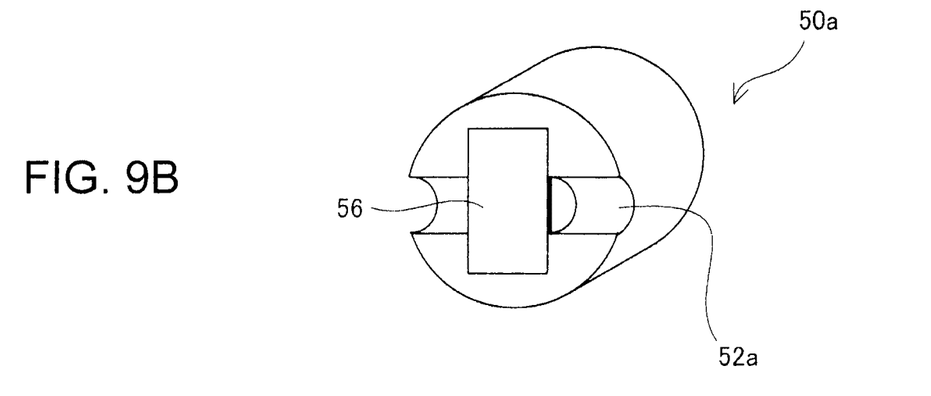
Figure 9C:
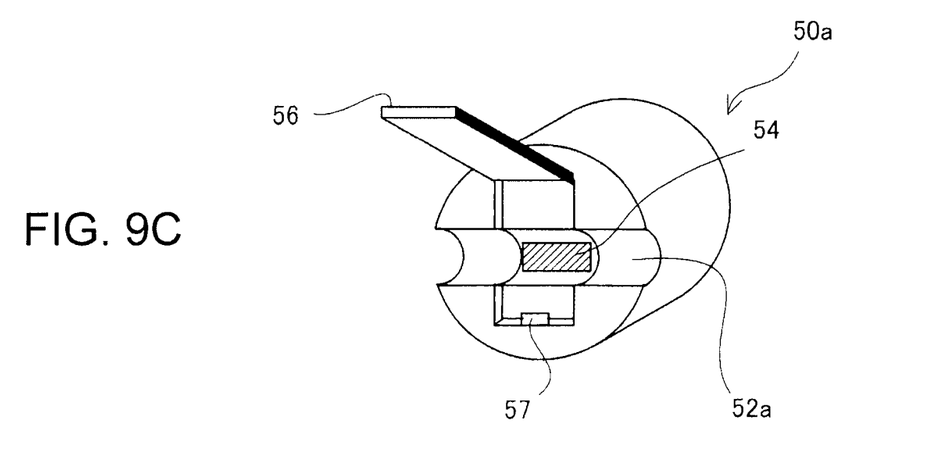

In the above embodiment, the flow path deforming mechanism 50 (FIGS. 3A and 3B, FIGS. 4A and 4B) is employed as a flow path deforming unit. However, various forms can be employed without being limited to the embodiment, as long as the internal pressure in the flow path can be changed by deformation of the flow path. FIGS. 9A to 9C are explanatory views showing a flow path deforming mechanism 50a as an example. The flow path deforming mechanism 50a holds and fixes the flow path 73 between a groove portion 52a and a movable portion 56 (see FIGS. 9A, 9B and 9C). As shown in FIG. 9C, the movable portion 56 is an open/close type. When the movable portion 56 is closed, a lock mechanism 57 (FIG. 9C) locks the movable portion 56.

As shown in FIG. 9C, the flow path deforming mechanism 50a has a pressing portion 54a and presses the flow path 73 under the control of the control unit 40. The drive mechanism of the pressing portion 54a is the same as the pressing mechanism 53 (FIGS. 4A and 4B) in the first embodiment and therefore will not be described further in detail. Such a configuration enables the flow path 73 to be easily taken out of the flow path deforming mechanism 50*a* even if the fluid supply apparatus 30 is stopped (for example, when power failure occurs) in the state where the flow path deforming mechanism 50*a* is pressing the flow path 73. In this way, the flow path deforming unit can take various forms. Also, the way of deforming the flow path 73 is not limited to pressing. Various forms of deformation to change the pressure inside the flow path such as expansion/contraction or bending of the flow path can be employed.

B3. Modification 3

Figure 10A:
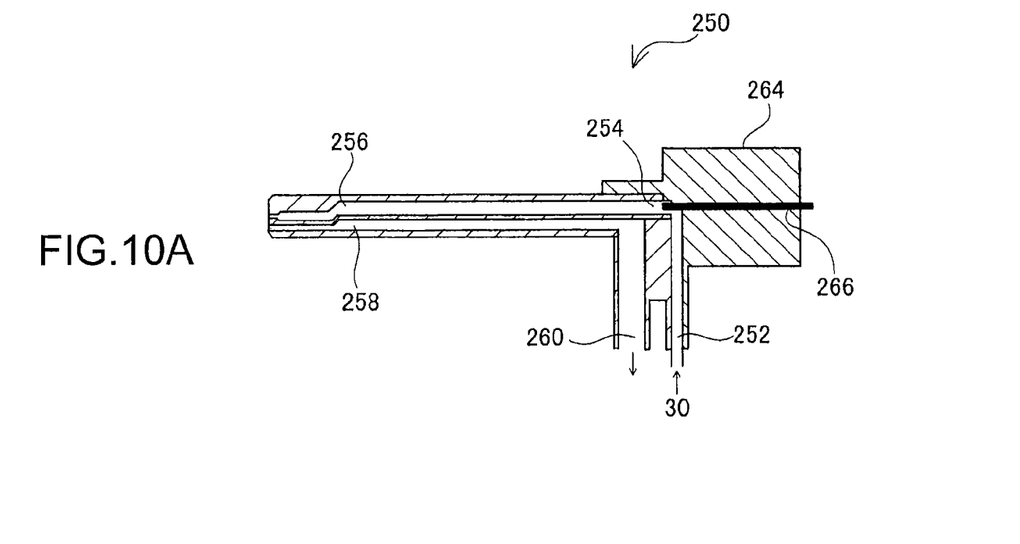
FIGS. 10A and 10B are explanatory views showing an example of a water jet knife that can be employed.
Figure 10B:
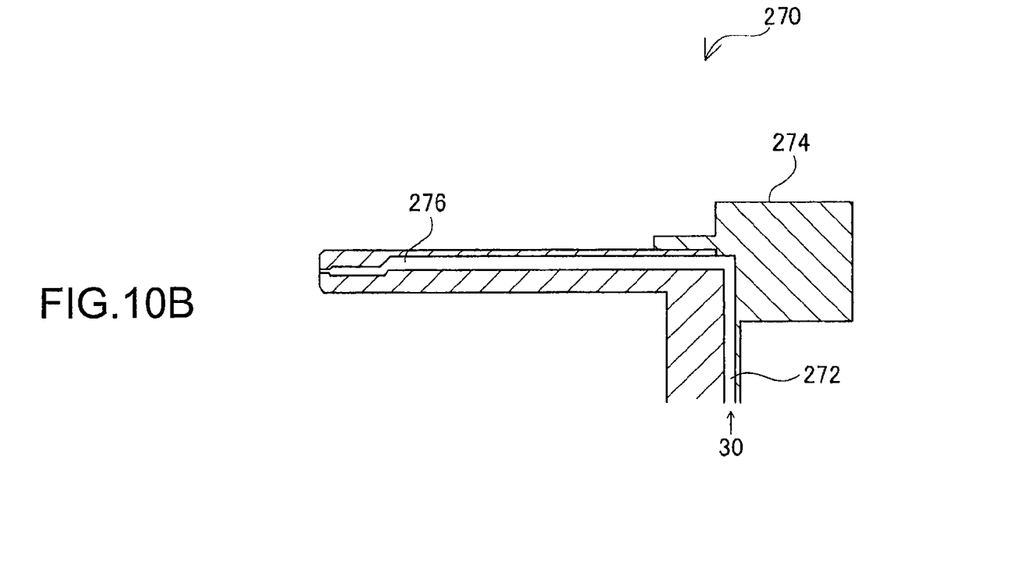

In the foregoing embodiments, the form of the water jet knife 20 described with reference to FIG. 7 is employed as a water jet knife. However, various forms of water jet knife may be employed without being limited to the embodiments. FIGS. 10A and 10B are explanatory views illustrating an example of a water jet knife that can be employed. FIG. 10A is an explanatory view illustrating the configuration of a water jet knife 250 utilizing a pulse laser. The water jet knife 250 has a suction path 252 for sucking in water from the fluid supply apparatus 30 via the flow path 73, an air bubble generating unit 254 which generates air bubbles in the water that is sucked in, and an ejection flow path 256 for ejecting the water. The water jet knife 250 also has a grip portion 264 for the user to hold the water jet knife 250, and an optical fiber 266.

The optical fiber 266 penetrates the grip portion 264 between the air bubble generating unit 254 and the outside. The optical fiber 266 extends outside of the grip portion 264 and is connected to a laser source (not shown). As a laser source, for example, a holmium-YAG laser (Ho-YAG laser: wavelength 2.1 μm) can be employed. The grip portion 264 supports the optical fiber 266 in the state where the distal end of the optical fiber 266 protrudes into the air bubble generating unit 254. The distal end of the optical fiber 266 protruding into the air bubble generating unit 254 is a pulse laser emission surface.

The water supplied from the fluid supply apparatus 30 circulates the flow path 73 and the suction path 252, then fills the air bubble generating unit 254, and is ejected outward via the air bubble generating unit 254 and the ejection flow path 256. As a pulse laser is emitted into the water from the distal end of the optical fiber 266 in the state where the air bubble generating unit 254 is filled with the water, the water absorbs the energy of the pulse laser and vaporizes instantaneously. Vapor bubbles are generated in the air bubble generating unit 254. With this generation of vapor bubbles, the internal pressure in the ejection flow path 256 rises quickly and the water inside the ejection flow path 256 is ejected outward from the ejection flow path 256 as a pulse jet. The ejection speed of the pulse jet thus ejected is, for example, 10 m/s to 80 m/s and is capable of excising tissues of human bodies or the like.

The water jet knife 250 also has a drain 260 connected to a suction pump (not shown). The drain 260 communicates with a suction flow path 258. For example, in a surgical operation, the water ejected from the ejection flow path 256 stays at the surgical site as a drain fluid. In this case, the water jet knife 250 can use the suction force of the suction pump to suck the drain fluid staying at the surgical site via the suction flow path 258.

With such a configuration, the water jet knife 250 can control the pulse jet PJ by laser emission.

FIG. 10B is an explanatory view illustrating a water jet knife 270 that can be employed as a water jet knife. The water jet knife 270 has a suction path 272 for sucking water supplied from the fluid supply apparatus 30 via the flow path 73, and an ejection flow path 276 for ejecting the sucked water. The distal end of the ejection flow path 276 is narrower than the inner part thereof. Therefore, the pressure of the water supplied from the fluid supply apparatus 30 is raised in the ejection flow path 276 and the water is ejected outward.

B4. Modification 4

In the foregoing embodiments, pressure fluctuation is restrained by deforming the flow path 73. However, pressure fluctuation may be restrained by deforming the flow path 71 and the flow path 72 at plural sites. That is, the fluid supply apparatus 30 may have plural flow path deforming units.

B5. Modification 5

In the foregoing embodiment, plunger pumps that carry out the feeding operation and the suction operation are employed as pumps. However, a pump that only carries out the feeding operation may be employed. Also in this case, control is performed in such a way that one pump carries out the feeding operation at any time. The control unit 40 drives the flow path deforming mechanism 50 at a timing correlated with the timing when each pump starts the feeding operation, and thus restrains the pressure fluctuation in the flow path. By taking this measure, fluctuation in the flow rate of water supplied can also be restrained.

B6. Modification 6

In the foregoing embodiment, the control unit 40 drives the flow path deforming mechanism 50 at a timing correlated with the timing when the pumps start the feeding operation. However, the timing of driving is not limited to this. If the timing when pressure fluctuation occurs inside the flow path due to a structural factor or external factor can be known in advance, the flow path deforming mechanism 50 may be driven at that timing. By doing so, internal pressure in the flow path can also be restrained. As a result, fluctuation in the flow rate can be restrained.

B7. Modification 7

The flow path deforming mechanism 50 is not limited to the function of pressing the flow path 73 for the purpose of pressure fluctuation restraint and may also have the function of a stop valve. For example, when the user carries out an operation to stop ejection of water from the water jet knife 20, the flow path deforming mechanism 50 may press the flow path 73 to block the flow path under the control of the control unit 40 so that the circulation of water is completely stopped. Then, as the user carries out an operation to start ejection of water from the water jet knife 20, the flow path deforming mechanism 50 may cancel the blocking of the flow path 73 and let the water circulate under the control of the control unit 40. Thus, when ejection of water from the water jet knife 20 is stopped, leakage of water staying inside the flow path from the nozzle of the water jet knife 20 can be restrained.

Also, the flow path deforming mechanism 50 may have the function of a safety valve. For example, when the user wants to stop the supply of water urgently without waiting for the operation of the plunger pumps to stop, the flow path deforming mechanism 50 may press and block the flow path 73 to stop the supply of water. In this case, an operation unit for causing the flow path deforming mechanism 50 to block the flow path 73 may be provided as an emergency stop switch. Thus, the supply of water can be stopped immediately.

The blocking of the flow path 73 by the flow path deforming mechanism 50 may also function as a safety lock. The user is to carry out a water ejection operation by first carrying out a flow path block canceling operation and then an ejection operation of the water jet knife 20. Thus, the fluid supply apparatus 30 can start ejecting water from the water jet knife 20 after making the user aware of the ejection of water.

B8. Modification 8

In the foregoing embodiment, water is employed as fluid. However, the fluid to be used is not limited to this. Various fluids such as low-viscosity oil can be employed.

B9. Modification 9

In the foregoing embodiments, a water jet knife is employed as a medical apparatus. However, the medical apparatus to be used is not limited to this. Various medical apparatuses, for example, a cleaner for cleaning an effected part in a surgical operation or treatment, and an apparatus for injecting a medical fluid into the body, can be employed.

What is claimed is:

1. A fluid supply apparatus which supplies fluid to a medical apparatus, comprising:
    a first pump capable of switching between suction of the fluid and ejection of the fluid;
    a second pump capable of switching between suction of the fluid and ejection of the fluid;
    a flow path which communicates with the first pump and the second pump and supplies the fluid to the medical apparatus; and
    a flow path deforming unit which deforms a part of the flow path;
    wherein the flow path deforming unit presses the flow path before the first pump switches to the state of sucking the fluid,
    wherein a speed at which the flow path deforming unit presses the flow path is the fastest when the first pump switches from the state of ejecting the fluid to the state of sucking the fluid.

2. The fluid supply apparatus according to claim 1, wherein the first pump ejects the fluid when the second pump sucks in the fluid,
    the second pump ejects the fluid when the first pump sucks in the fluid, and
    the flow path deforming unit cancels the pressing on the flow path before the first pump switches from the state of sucking the fluid to the state of ejecting.

3. The fluid supply apparatus according to claim 1, wherein an amount of deformation of the flow path by the flow path deforming unit is at a maximum during a period from when an amount of ejection per unit time by the first pump reaches a predetermined amount of fluid fed, until the amount of ejection per unit time becomes smaller than the predetermined amount of ejection.

4. The fluid supply apparatus according to claim 1, wherein the second pump switches from the suction to the ejection when the first pump switches from the state of ejecting the fluid to the state of sucking the fluid.

5. The fluid supply apparatus according to claim 4, wherein, where one cycle from when the first pump ejects the fluid until the suction of the fluid ends is T, a deformation period during which the flow path deforming unit presses the flow path is T/2 or shorter.

6. The fluid supply apparatus according to claim 1, wherein the flow path deforming unit deforms the flow path by pressing an outer wall surface of the flow path.

7. The fluid supply apparatus according to claim 1, wherein the flow path includes a first flow path connected to the first pump, a second flow path connected to the second pump, and a third flow path that is a flow path into which the first flow path and the second flow path join together, and
    the flow path deforming unit presses the third flow path.

8. The fluid supply apparatus according to claim 1, wherein the flow path deforming unit presses the flow path to block the flow path, and thus stops supply of the fluid from the first pump and the second pump to the medical apparatus.

9. The fluid supply apparatus according to claim 1, wherein the medical apparatus is a therapeutic apparatus which ejects the fluid to the living body and thus treats the living body.

10. A fluid supply apparatus which supplies fluid to a medical apparatus, comprising:
    a pump mechanism having plural pumps capable of ejecting the fluid outside;
    a flow path which is elastic and supplies the fluid ejected from each of the pumps to the medical apparatus; and
    a flow path deforming unit which presses the flow path at a predetermined timing that is set in advance,
    wherein a speed at which the flow path deforming unit presses the flow path is the fastest when a first pump of the plural pumps switches from a state of ejecting the fluid.

11. A control method for a fluid supply apparatus which supplies fluid to a medical apparatus, the fluid supply apparatus including
    a first pump which alternately carries out suction and ejection of the fluid,
    a second pump which alternately carries out suction and ejection of the fluid,
    a flow path which communicates with the first pump and the second pump and supplies the fluid, and
    a flow path deforming unit which deforms a part of the flow path,
    the method comprising:
    causing the second pump to eject the fluid when the first pump sucks in the fluid;
    causing the first pump to eject the fluid when the second pump sucks in the fluid; and
    causing the flow path deforming unit to start first pressing on the flow path before the first pump switches from the state of ejecting the fluid to the state of sucking the fluid, and to start second pressing on the flow path when the second pump carries out the ejection,
    wherein a speed at which the flow path deforming unit presses the flow path is the fastest when the first pump switches from the state of ejecting to the state of sucking.

12. The control method for the fluid supply apparatus according to claim 11, wherein an amount of deformation of the flow path by the flow path deforming unit has a peak during a period from when an amount of ejection per unit time by the first pump reaches a predetermined amount of ejection, until the amount of ejection per unit time becomes smaller than the predetermined amount of ejection.

13. The control method for the fluid supply apparatus according to claim 11, wherein the second pump switches from the state of sucking to the state of ejecting when the first pump switches from the state of ejecting to the state of sucking.

14. The control method for the fluid supply apparatus according to claim 13, wherein, where one cycle from when the first pump starts the ejection until the suction ends is T, a deformation period during which the flow path deforming unit presses the flow path is T/2 or shorter.

15. The control method for the fluid supply apparatus according to claim 11, wherein the flow path deforming unit deforms the flow path by pressing an outer wall surface of the flow path.

\* \* \* \* \*